United States Patent
Lewis et al.

(10) Patent No.: US 10,641,754 B2
(45) Date of Patent: May 5, 2020

(54) SYSTEM AND METHOD FOR DETERMINATION OF UNUSABLE PRODUCTS

(71) Applicant: Walmart Apollo, LLC, Bentonville, AR (US)

(72) Inventors: Steven J. Lewis, Bentonville, AR (US); Nicholaus A. Jones, Fayetteville, AR (US); Matthew D. Biermann, Fayetteville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 0 days.

(21) Appl. No.: 15/873,322

(22) Filed: Jan. 17, 2018

(65) Prior Publication Data
US 2018/0238848 A1   Aug. 23, 2018

Related U.S. Application Data

(60) Provisional application No. 62/462,404, filed on Feb. 23, 2017.

(51) Int. Cl.
*G06K 9/00* (2006.01)
*G01N 33/02* (2006.01)
(Continued)

(52) U.S. Cl.
CPC ......... *G01N 33/02* (2013.01); *G06K 9/00671* (2013.01); *G06Q 30/0623* (2013.01); *H04W 4/35* (2018.02); *G06K 2209/17* (2013.01)

(58) Field of Classification Search
CPC .......... G01N 33/02; G01N 2021/8466; G01N 2223/618; G06K 2209/17; G06T 2207/30128
See application file for complete search history.

(56) References Cited

U.S. PATENT DOCUMENTS 5,914,665 A   6/1999   Thorp
6,072,121 A   6/2000   Penczak
(Continued)

FOREIGN PATENT DOCUMENTS

WO   2015200782   12/2015

OTHER PUBLICATIONS

PCT; App. No. PCT/US2018/014194; International Search Report and Written Opinion dated May 15, 2018.
(Continued)

*Primary Examiner* — Avinash Yentrapati
(74) *Attorney, Agent, or Firm* — Fitch, Even, Tabin & Flannery LLP

(57) ABSTRACT

A credibility weight for each of a plurality of users is stored and is associated with a reliability of the user in accurately indicating whether the products have become spoiled. Images of a plurality of products at a retail store are received and electronically arranged in an organized pattern. The organized pattern is rendered onto selected ones of a plurality of display devices. Electronic choices from selected ones of the plurality of the users are received. Each of the electronic choices indicates for a selected one of the plurality of products whether the selected user believes the selected product has spoiled or has become unusable. A spoilage score for each product of the products is determined. A control signal is transmitted to a receiver circuit at the retail store instructing a human or robot to perform an investigation when the spoilage score exceeds a predetermined threshold.

14 Claims, 3 Drawing Sheets

(51) Int. Cl.
*G06Q 30/06* (2012.01)
*H04W 4/35* (2018.01)

(56) References Cited

U.S. PATENT DOCUMENTS

| | | |
|---|---|---|
| 6,242,697 B1 | 6/2001 | Gerken |
| 6,316,725 B1 | 11/2001 | Cole |
| 6,401,400 B1 | 6/2002 | Elliott |
| 6,487,091 B2 | 11/2002 | Malkowski, Jr. |
| 6,795,320 B2 | 9/2004 | Malkowski, Jr. |
| 7,234,674 B2 | 6/2007 | Rippel |
| 7,243,810 B2 | 7/2007 | O'Brien |
| 7,248,888 B2 | 7/2007 | Inselberg |
| RE40,069 E | 2/2008 | Cole |
| 7,353,961 B2 | 4/2008 | Hull |
| 7,432,439 B2 | 10/2008 | Takada |
| 7,432,442 B2 | 10/2008 | Peck |
| 7,575,122 B2 | 8/2009 | Hull |
| 7,731,045 B2 | 6/2010 | Harpenau |
| 7,812,255 B2 | 10/2010 | Garvin |
| 7,838,769 B2 | 11/2010 | Peck |
| 7,881,960 B2 | 2/2011 | Ramamurti |
| 7,922,020 B2 | 4/2011 | Wronski |
| 8,003,889 B2 | 8/2011 | Turcovsky |
| 8,026,443 B1 | 9/2011 | Czarnecki |
| 8,376,592 B2 | 2/2013 | Engstrom |
| 8,567,029 B2 | 10/2013 | Oymaian |
| 8,756,121 B2 | 6/2014 | Gonsalves |
| 8,933,331 B1 | 1/2015 | Gretz |
| 8,933,350 B1 | 1/2015 | Gretz |
| 9,029,716 B2 | 5/2015 | Lupsa |
| 9,094,670 B1 | 7/2015 | Furio |
| 9,117,239 B2 | 8/2015 | Kubicki |
| 9,169,969 B2 | 10/2015 | Buckley |
| 10,009,667 B2* | 6/2018 | Taylor ..................... H04Q 9/00 |
| 10,216,175 B2* | 2/2019 | Enssle ................ G06F 16/2457 |
| 2005/0131723 A1 | 6/2005 | Sholl |
| 2009/0242631 A1* | 10/2009 | Wishnatzki ............ G06Q 10/08 235/385 |
| 2011/0035299 A1 | 2/2011 | Casey |
| 2011/0295722 A1* | 12/2011 | Reisman ............ G06Q 30/0201 705/27.1 |
| 2014/0268801 A1 | 9/2014 | Madden |
| 2014/0273557 A1 | 9/2014 | Cartier, Jr. |
| 2014/0304654 A1* | 10/2014 | Gross .................... G06F 3/0482 715/811 |
| 2015/0127438 A1 | 5/2015 | Wedderburn |
| 2015/0381968 A1 | 12/2015 | Arora |
| 2016/0170996 A1* | 6/2016 | Frank ................ G06F 16/24578 707/748 |
| 2018/0106742 A1* | 4/2018 | Wilkinson .............. G01M 3/00 |

OTHER PUBLICATIONS

Godoy, Maria; "Wal-Mart, America's Largest Grocer, is Now Selling Ugly Fruit and Vegetables"; https://www.npr.org/sections/thesalt/2016/07/20/486664266/walmart-world-s-largest-grocer-is-now-selling-ugly-fruit-and-veg; Jul. 20, 2016; pp. 1-4.

Peng, Yankun et al.; "Optical Methods and Techniques for Meat Quality Inspection"; vol. 58(5); Transactions of the ASABE (American Society of Agricultural and Biological Engineers); Jul. 2015; pp. 1371-1386.

RSIP Vision; "Grading and Sorting"; https://www.rsipvision.com/grading-and-sorting/; Available on Wayback Machine as of Jun. 23, 2017; pp. 1-8.

\* cited by examiner

SYSTEM AND METHOD FOR DETERMINATION OF UNUSABLE PRODUCTS

CROSS-REFERENCE TO RELATED APPLICATION

This application claims the benefit of the following U.S. Provisional Application No. 62/462,404 filed Feb. 23, 2017, which is incorporated herein by reference in its entirety.

TECHNICAL FIELD

This invention relates generally determining whether products are unusable or spoiled, and more particularly, to making such a determination based upon the inputs of multiple users.

BACKGROUND

Retail stores carry a wide variety of products. Some of these products spoil or become otherwise unusable over time.

To take one example, a grocery store typically has various types of produce that is available for purchase. For instance, most grocery store sell fruit and vegetables. However, over time this produce becomes spoiled and unusable. If the products are not removed after they have become spoiled, it is possible that the products are purchased and consumed by customers. This can lead to problems such as consumers becoming ill after ingesting the product, the customer developing a negative impression of the shopping experience or the retail store, and/or reduced sales for the store.

In one particular example of these problems, online orders of produce are supported by some retail stores. However, some spoiled produce may be present in the bins of the store. This bad produce can be selected by employees of the store to fulfill online orders. Consequently, some produce picked for online orders may be unsatisfactory to customers, and, as a result, some customers may be reluctant to order produce online, and sales at the retail store are lost or reduced.

Current approaches for removing unusable products rely upon store employees to manually monitor the condition of the products. Unfortunately, store employees typically have many more tasks to perform, sometimes forgetting to monitor the products, or only occasionally monitor the products. Further, spoilage of products often occurs quickly requiring employees to remove the product quickly and not wait for a convenient time to perform the removal. All of these problems leads to spoiled products being present and available to customers for purchase.

BRIEF DESCRIPTION OF THE DRAWINGS

Disclosed herein are embodiments of systems, apparatuses and methods pertaining to determining whether a product is unusable or spoiled. This description includes drawings, wherein.

Figure 1:
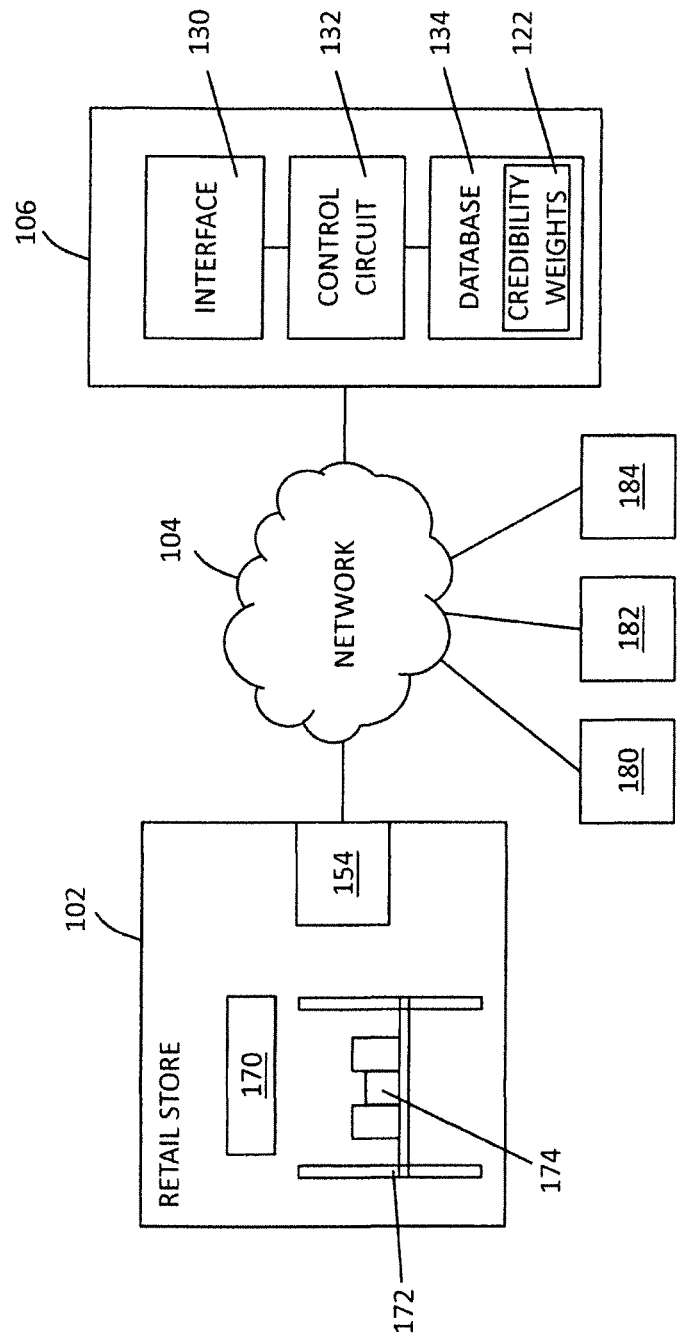
FIG. 1 is a block diagram showing a system for determining whether a product is unusable or spoiled in accordance with some embodiments.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, systems, apparatuses and methods are provided that identify unusable products from a retail store. More specifically, a plurality of users together determine whether a product is spoiled or has otherwise become unusable. In making the determination, the credibility of each of the users making selections is considered.

These approaches may be implemented as an electronic game that is accessed by the plurality of users. The game can be played at any time and, preferably, from any location where electronic devices can be used and access computer networks.

In many of these embodiments, a system that is configured to determine whether products have become spoiled or unusable based upon inputs received from a plurality of users, includes a network, a plurality of display devices, a receiver circuit, a database, an interface, and a control circuit.

The plurality of display devices is coupled to the network, and the receiver circuit is disposed at a retail store. The database is configured to store a credibility weight for each of a plurality of users. The credibility weight being associated with a reliability of the user in accurately indicating whether the products have become spoiled or unusable.

The interface is disposed at a central processing center and is configured to receive images of a plurality of products at the retail store. The interface is coupled to the network.

The control circuit is coupled to the interface and the database. The control circuit is disposed at the central processing center, and is configured to electronically arrange the received images in an organized pattern. The control circuit is additionally configured to render the organized pattern onto selected ones of the display devices via the interface and the network.

The control circuit is configured to responsively receive electronic choices from selected ones of the plurality of the users via the interface and network. Each of the electronic choices indicates for a selected one of the plurality of products whether the selected user believes the selected product has spoiled or has become unusable. The control circuit is further configured to determine a spoilage score for each product of the plurality of products. The spoilage score is a summation of credibility weights for each user that indicates spoilage for a product. The control circuit is additionally configured to transmit a control signal to the receiver circuit at the retail store instructing a human or robot to perform an investigation when the spoilage score exceeds a first predetermined threshold.

In aspects, the spoilage score can also be weighted by other factors For example, the control circuit may be configured to further weight the spoilage score by a factor related to a type of product, a factor related to a cost of the product, a factor related to a number of the plurality of users, a factor related to a number of users having credibility weights exceeding a second predetermined threshold, or a factor related to the number of users having a credibility weight below a third predetermined threshold.

In other examples, a store employee lowers a price of selected ones of the plurality of products based upon the investigation.

In yet other examples, various organized patterns can be used. For example, the organized pattern may be a matrix.

In aspects, the credibility weight of the selected user is adjusted after the investigation. In other examples, the adjustment is increasing the credibility weight. In yet other examples, the adjustment is decreasing the credibility weight.

In others of these embodiments, a credibility weight for each of a plurality of users is stored, for example, in a database. The credibility weight is associated with a reliability of the user in accurately indicating whether the products have become spoiled or unusable.

At a central processing center, images of a plurality of products at a retail store are received and electronically arranged in an organized pattern. The organized pattern is rendered onto selected ones of a plurality of display devices. Electronic choices from selected ones of the plurality of the users are received. Each of the electronic choices indicates for a selected one of the plurality of products whether the selected user believes the selected product has spoiled or has become unusable. A spoilage score for each product of the plurality of products is determined. The spoilage score is a summation of credibility weights for each user that indicates spoilage for a product. A control signal is transmitted to a receiver circuit at the retail store instructing a human or robot to perform an investigation when the spoilage score exceeds a first predetermined threshold.

Referring now to FIG. 1, one example of a system 100 for determining whether a product is spoiled or unusable is described. The retail store 102 may be any type of retail store, for example, a discount center, a grocery store, a department store, or a hardware store to mention a few examples.

The retail store 102 includes a database 152. A communication device 154 allows the retail store 102 to communicate with devices and entities that are external to the store. The communication device 154 may include any combination of hardware or software that allows communications to be received at the retail store 102 (the communication device 154 may include a receiver circuit), and makes transmissions from the retail store 102 (a transmitter circuit). In one example, the communication device 154 may be a transceiver circuit (include both a transmitter circuit and a receiver circuit). The communication device 154 may be deployed within or at another device (e.g., a modem, a smart phone, or a personal computer, to mention a few examples). The communication device 154 may transmit images obtained by a sensor 170 of products 174 on a shelf 172 in the retail store.

The sensor 170 may be any type of sensing device. In aspects, the sensor 170 is a camera that obtains visible images. The shelf 172 may be any type of storage device (e.g., a shelf, a bin, any type of storage unit or structure to mention a few examples) that presents the products 174 to customers. The products 174 may be any type of product such as produce (apples, oranges, bananas), meat, milk, cheese, eggs, packaged dry goods, to mention a few examples.

Cloud network 104 is coupled to the communication device 154 (e.g., a transceiver) at the retail store 102. The cloud network 104 may be any type of computer or communication network and may include routers, gateways, and servers to mention a few examples of devices that can form or be utilized in the network 104. The cloud network 104 may also be combinations of various types of networks.

Display devices 180, 182, and 184 are coupled to the network 104. The display devices 180, 182, and 184 are any type of device that can render a visual image to a user. For example, the display devices 180, 182, and 184 may be smart phones, personal computers, laptops, or tablets. The display devices 180, 182, and 184 may be at different locations and operated by different user.

A plurality of users at the user devices 180, 182, and 184 together determine whether any of the products 174 have spoiled or have otherwise become unusable. In making the determination, the credibility of each of the users making selections is considered. These approaches may be implemented as an electronic game that is accessed by the plurality of users at the user devices 180, 182, and 184. The game can be played at any time, for any duration, and, preferably, from any location where electronic devices can be used and access the network 104.

The apparatus 106 includes an interface 130, a control circuit 132, and a database 134. The apparatus 106 may be deployed at a central processing or control center. The interface 130 is configured to receive from the retail store 102 the images associated with the products 174 and communications to and from the display devices 180, 182, and 184. The database 134 stores a plurality of credibility weights 122 for each of a plurality of users. Each credibility weight 122 is associated with a reliability of one user in accurately indicating whether the products have become spoiled or unusable.

The apparatus 106 is configured to manage the execution of the game. For example, the database 134 may store account information for users that wish to play the game. In aspects, the control circuit 132 may execute and maintain various security procedures that ensure that only authorized users can play the game.

It will be appreciated that as used herein the term "control circuit" refers broadly to any microcontroller, computer, or processor-based device with processor, memory, and programmable input/output peripherals, which is generally designed to govern the operation of other components and devices. It is further understood to include common accompanying accessory devices, including memory, transceivers for communication with other components and devices, etc. These architectural options are well known and understood in the art and require no further description here. The control circuit 132 may be configured (for example, by using corresponding programming stored in a memory as will be well understood by those skilled in the art) to carry out one or more of the steps, actions, and/or functions described herein.

The control circuit 132 is coupled to the interface 130 and the database 134. The control circuit 132 is disposed at the central processing center, and is configured to electronically arrange the received images in an organized pattern. The control circuit 132 is additionally configured to render the organized pattern onto selected ones of the display devices 180, 182, and 184 via the interface 130 and the network 104.

The control circuit 132 is configured to responsively receive electronic choices from selected ones of the plurality of the user devices 180, 182, and 184 via the interface 130 and network 104. Each of the electronic choices indicates for a selected one of the plurality of products 174 whether the selected user believes the selected product has spoiled or has become unusable. In examples, the electronic choices may be made by a user clicking on an image of a product to indicate that the product has spoiled (according to the opinion of the user). In other examples, the electronic choices may be indicated by a user entering a number.

The control circuit 132 is further configured to determine a spoilage score for each product of the plurality of products 174. The spoilage score is a summation of credibility weights 122 for each user that indicates spoilage for a product. The control circuit 132 is additionally configured to transmit a control signal to the receiver circuit 154 at the retail store 102 instructing a human or robot to perform an investigation when the spoilage score exceeds a first predetermined threshold.

In aspects, the spoilage score can also be weighted by other factors besides the credibility of a user. For example, the control circuit 132 may be configured to further weight the spoilage score by a factor related to a type of product, a factor related to a cost of the product, a factor related to a number of the plurality of users, a factor related to a number of users having credibility weights 122 exceeding a second predetermined threshold, or a factor related to the number of users having a credibility weight below a third predetermined threshold.

In other examples, a store employee lowers a price of selected ones of the plurality of products 174 based upon the investigation. For example, when the product is produce and the employee determines the product is still fit to be sold, the employee may lower the price of the produce in an attempt to quickly sell the products. In aspects, the credibility weight 122 of the selected user is adjusted after the investigation. In other examples, the adjustment is increasing the credibility weight 122. In yet other examples, the adjustment is decreasing the credibility weight 122.

In yet other examples, various organized patterns can be used. For example, the organized pattern may be a square matrix. Other patterns (e.g., circles, triangles, or various polygons) can also be utilized.

Figure 2:
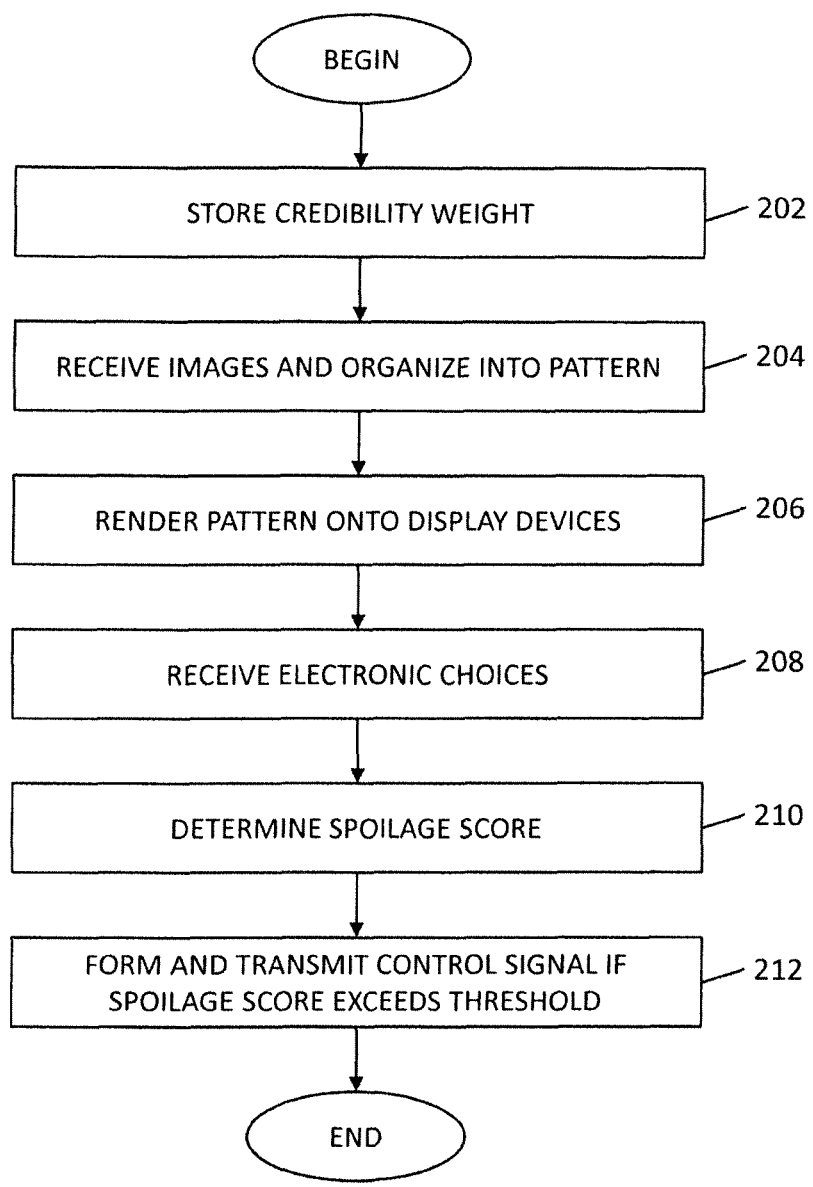
FIG. 2 is a flow chart showing an approach for determining whether a product is unusable or spoiled in accordance with some embodiments.

Referring now to FIG. 2, one example of an approach for determining whether products are unusable or spoiled is described. At step 202, a credibility weight for each of a plurality of users is stored, for example, in a database. The credibility weight for each of these users may be entered by a user.

The credibility weight is associated with a reliability of the user in accurately indicating whether the products have become spoiled or unusable. The credibility weight may be fixed or it may change over time. For example, a determination may be made (e.g., by an employee of the retail store) whether the user was correct in selecting a bad product. If the user was correct, their credibility weight may be increased. If the user was incorrect, their credibility weight may be decreased.

At step 204 and at a central processing center, images of a plurality of products at a retail store are received and electronically arranged in an organized pattern. The products may be of one type (e.g., apples) or of different types (e.g., apples, bananas, and oranges). The organized pattern may be a matrix of squares in one example where each of the squares is an image of a different product. Other convenient patterns (e.g., circles, semi-circles, polygons, and so forth) may also be used.

At step 206, the organized pattern is rendered onto selected ones of a plurality of display devices. In examples, images of the products may be displayed as a matrix of boxes. For example, apples in the produce section of a grocery store may be shown in a square matrix of boxes, with each box displaying an image of a different apple.

At step 208, electronic choices from selected ones of the plurality of the users are received. Each of the electronic choices indicate for a selected one of the plurality of products whether the selected user believes the selected product has spoiled or has become unusable.

At step 210, a spoilage score for each product of the plurality of products is determined. The spoilage score is a summation of credibility weights for each user that indicates spoilage for a product. To take one example, if user A (with credibility weight 0.9) indicates a product is bad, user B thinks the same product is good, and user C (with weight 0.2) thinks the same product is bad, the summation is 0.9+0.2=1.1. If the summation exceeds a threshold value, then the product is considered to be "bad," and an action can be taken such as lowering the price or the item, or removing the item from the shelf At step 212, a control signal is formed and transmitted to a receiver circuit at the retail store instructing a human or robot to perform an investigation when the spoilage score exceeds a first predetermined threshold. For example, if in the previous example the threshold is 1.0, then a control signal is transmitted since 1.1 is greater than 1.0.

The control signal may be in the form of a message to the employee. In other examples, the control signal comprises electronic instructions (according to any format or protocol) that cause an automated vehicle (e.g., an automated ground vehicle or aerial drone) to proceed to the product. In aspects, the control signal may include the coordinates or location of the product within the store. In other aspects, the control signal may include or identify an action to take (e.g., remove the product, change the price of the product, or change the price of the product to a particular value).

Figure 3:
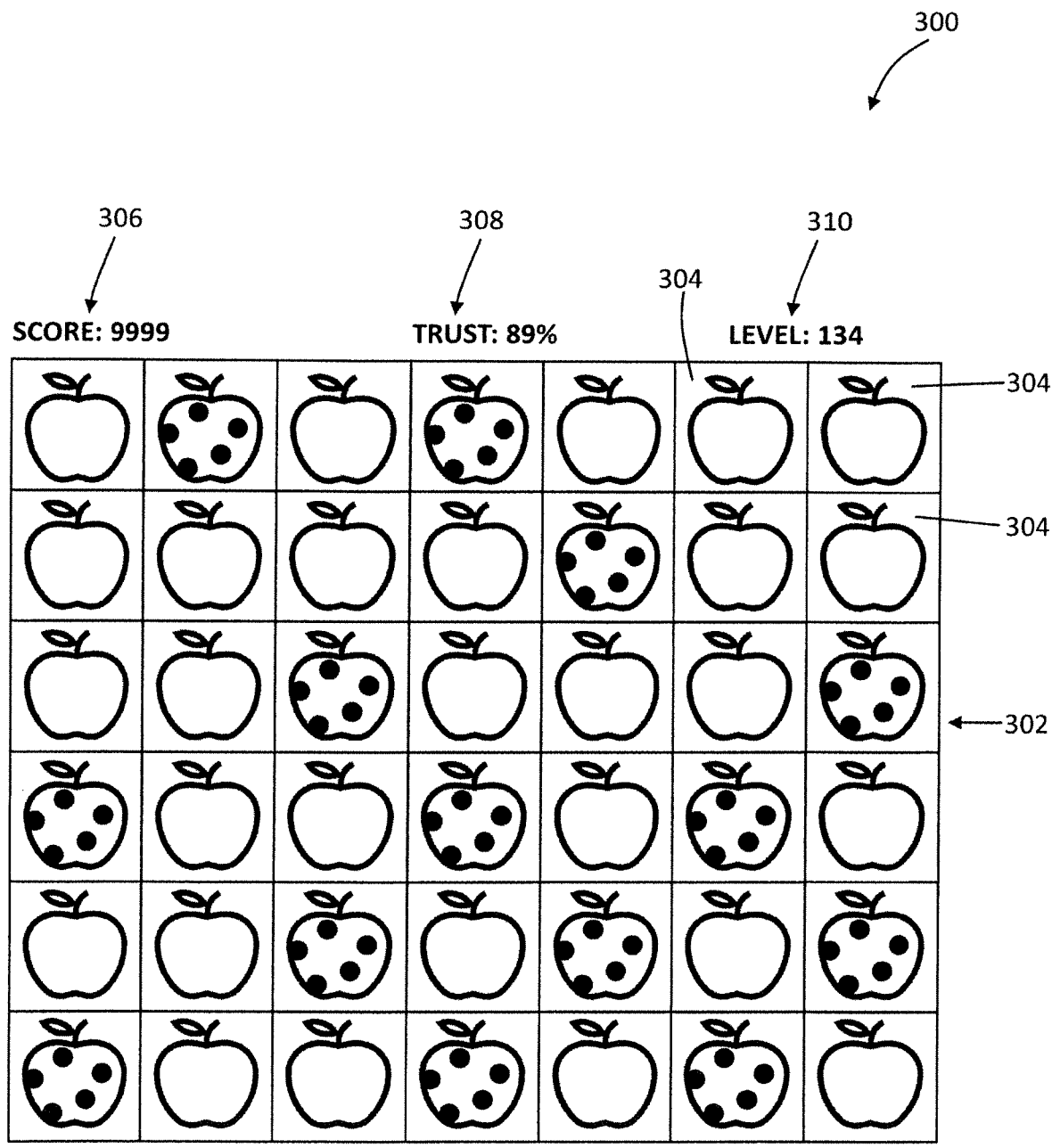
FIG. 3 is a block diagram showing a display of a matrix utilized by a user to select products that are unusable or spoiled in accordance with some embodiments.

Referring now to FIG. 3, one example of an organized pattern 302 of products visually rendered as a display 300 to a user is described. The organized pattern 302 is presented as a game to users. The display 300 may be rendered to a user on any number of devices such as on a screen at a smart phone, a personal computer, a laptop computer, or a tablet. Each user may have an account and the game is played by the user logging into their account.

In aspects, the organized pattern 302 includes a grid or matrix of boxes 304 (only some of the boxes are labeled "304" for clarity in the drawings). Each of the boxes 304 includes an image of a piece of produce, in this case, an apple. In some approaches, other features are provided allowing a user to zoom in on a particular image, obtain a new (e.g., better) picture of the produce, or rotate the image to view a different side of a particular piece of produce.

The display 300 also includes a score field 306. The score field 306 includes a score of points accumulated by the individual user while playing the game. In this example, the user has accumulated 9999 points.

The display 300 also includes a trust factor field 308. The trust factor field 308 includes a percentage value showing the trust factor enjoyed by the user. In this example, the trust factor is 89% indicating that the user is assumed to be correct (or trusted) 89% of the time.

The display 300 also includes a level field 310. The level field 310 may represent the playing level obtained by the user. In the example, the level is 134.

In aspects, the game is playable online by users and the display 300 is presented to the users to allow a user to choose which (if any) of the produce shown in the boxes 304 is bad, spoiled, or unusable produce. The user may indicate their selection in a wide variety of different ways. For example, the boxes may have or be associated with hyperlinks, which the user may click on (with a computer mouse) to select one of the boxes. In other examples, the boxes may be numbered and the user may enter the number of a piece of produce via a keypad.

In some examples, a consensus protocol is created by having the same display of produce presented to (and played) by multiple users. In other examples, the same display is presented to multiple users having the same trust factor or being with a predetermined range of trust factors. In still other examples, displays that are played by users with a high trust factor (e.g., a trust factor above a predetermined value) will require less users to play the same map.

In other aspects, for users who regularly correctly choose the bad produce in majority consensus with others, that user is assigned a "trust" factor (tied to their account) that increases over time. On the other hand, for users who regularly incorrectly choose the bad produce in majority consensus with others, that particular user is assigned a "trust" factor tied to their account that decreases over time.

Once a threshold of trust and consensus is made on bad produce selected, an alert can be generated and acted upon for in person inspection. For example, a human or automated vehicle may be sent to remove the produce.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A system that is configured to determine whether products have become spoiled or unusable based upon inputs received from a plurality of users, the system comprising:
    a network;
    a plurality of display devices coupled to the network, each of the plurality of display devices operated by a plurality of users to execute a computer game;
    a transceiver circuit disposed at a retail store and coupled to the network;
    a sensor disposed at the retail store and coupled to the transceiver circuit, the sensor being configured to obtain images of a plurality of products at the retail store;
    a database that is configured to store a plurality of separate credibility weights for the plurality of users, the credibility weights being associated with a reliability of each user in accurately indicating whether the products have become spoiled or unusable, wherein the credibility weights change over time based upon accuracy of predictions;
    a control circuit that is coupled to the network and the database, the control circuit being disposed at the central processing center and configured to receive the images of the plurality of products obtained by the sensor at the retail store via the transceiver circuit and network, the control circuit configured to execute the computer game for each of the users, wherein execution of the computer game causes the control circuit to:
    electronically arrange the received images in an organized pattern;
    render the organized pattern onto the display devices via the network such that each of the different users views the organized pattern on their respective display device;
    responsively receive choices from the users, each of the choices indicating for a selected one of the plurality of products whether the selected user believes the selected product has spoiled or has become unusable;
    determine a spoilage score for each product of the plurality of products, the spoilage score being a numeric summation of credibility weights for each of the users that indicates spoilage for a product;
    comparing the spoilage score to a first predetermined threshold;
    transmit a control signal to the transceiver circuit at the retail store instructing a robot to perform an investigation when the spoilage score exceeds the first predetermined threshold, the control signal causing the robot to navigate through the retail store to the location of the products to perform the investigation;
    such that execution of the game by the users collectively determines whether each product from the plurality of products has spoiled.

2. The system of claim 1, wherein the control circuit is configured to further weight the spoilage score by a factor selected from the group consisting of: a factor related to a type of product, a factor related to a cost of the product, a factor related to a number of the plurality of users, a factor related to a number of users having credibility weights exceeding a second predetermined threshold, a factor related to the number of users having a credibility weight below a third predetermined threshold.

3. The system of claim 1, wherein a store employee lowers a price of selected ones of the plurality of products based upon the investigation.

4. The system of claim 1, wherein the organized pattern is a matrix.

5. The system of claim 1, wherein the credibility weight of the selected user is adjusted after the investigation.

6. The system of claim 5, wherein the adjustment is increasing the credibility weight.

7. The system of claim 5, wherein the adjustment is decreasing the credibility weight.

8. A method to determine whether products have become spoiled based upon inputs received from a plurality of users, the method comprising:
    providing a plurality of display devices operated by a plurality of users, each of the display devices being operated to execute a computer game;
    storing a plurality of separate credibility weights for the plurality of users, the credibility weights being associated with a reliability of each user in accurately indicating whether the products have become spoiled or unusable, wherein the credibility weights change over time based upon accuracy of predictions;
    at a control circuit at a central processing center, receiving images of a plurality of products at a retail store, the images being obtained by a sensor at the retail store, the control circuit also executing the computer game for each of the users, wherein execution of the computer game causes the control circuit to:
    electronically arrange the received images in an organized pattern, render the organized pattern onto a plurality of display devices such that each of the different users views the organized pattern on their respective display device, responsively receive choices from the users electronic choices from the users, each of the choices indicating for a selected one of the plurality of products whether the selected user believes the selected product has spoiled or has become unusable, determine a spoilage score for each product of the plurality of products, the spoilage score being a numeric summation of credibility weights for each user that indicates spoilage for a product, compare the spoilage score to a first predetermined threshold, transmit a control signal to a transceiver circuit at the retail store instructing a robot to perform an investigation when the spoilage score exceeds the first predetermined threshold, the control signal causing the robot to navigate through the retail store to the location of the products to perform the investigation, such that execution of the game by the users collectively determines whether each product from the plurality of products has spoiled.

9. The method of claim 8, further comprising weighting the spoilage score by a factor selected from the group consisting of: a factor related to a type of product, a factor related to a cost of the product, a factor related to a number of the plurality of users, a factor related to the number of users having credibility weights exceeding a second predetermined threshold, a factor related to the number of users having a credibility weight below a third predetermined threshold.

10. The method of claim 8, further comprising lowering a price of selected ones of the plurality of products as a result of the investigation.

11. The method of claim 8, wherein the organized pattern is a matrix.

12. The method of claim 8, wherein the credibility weight of the selected user is adjusted after the investigation.

13. The method of claim 12, wherein the adjustment is increasing the credibility weight.

14. The method of claim 12, wherein the adjustment is decreasing the credibility weight.

\* \* \* \* \*